United States Patent [19]

Murray et al.

[11] Patent Number: 5,451,395
[45] Date of Patent: * Sep. 19, 1995

[54] HAIR TREATMENT COMPOSITION

[75] Inventors: Andrew M. Murray, South Wirral; Joanne M. de Groot, Wirral, both of England

[73] Assignee: Chesebrough-Pond's USA Co., Division of Conopco, Inc., Greenwich, Conn.

[*] Notice: The portion of the term of this patent subsequent to Jan. 4, 2011 has been disclaimed.

[21] Appl. No.: 125,049

[22] Filed: Sep. 21, 1993

Related U.S. Application Data

[63] Continuation of Ser. No. 753,510, Sep. 3, 1991, Pat. No. 5,275,808.

[30] Foreign Application Priority Data

Sep. 3, 1990 [GB] United Kingdom ............... 90309623

[51] Int. Cl.$^6$ ............................................. A61K 7/075
[52] U.S. Cl. .............................. 424/70.11; 424/70.1; 424/70.21; 424/70.22; 424/70.27; 424/70.31; 514/880; 514/881
[58] Field of Search ............. 424/70, 71, 70.11, 70.21, 424/70.22, 70.27, 70.31; 514/723, 880, 881

[56] References Cited

U.S. PATENT DOCUMENTS

| | | | |
|---|---|---|---|
| 3,972,998 | 8/1976 | Keiner | 424/70 |
| 4,013,786 | 3/1977 | Cella et al. | 424/70 |
| 4,062,939 | 12/1977 | Scott | 424/70 |
| 4,176,176 | 11/1979 | Cella et al. | 424/70 |
| 4,183,367 | 1/1980 | Goebel et al. | 132/7 |
| 4,184,973 | 1/1980 | Shaw | 424/70 |
| 4,399,077 | 8/1983 | Vanlerberghe et al. | 260/501.13 |
| 4,584,196 | 4/1986 | Vanlerberghe et al. | 424/70 |
| 4,765,975 | 8/1988 | Iovanni et al. | 424/70 |
| 4,778,675 | 10/1988 | Vanlerberghe et al. | 424/70 |
| 4,803,067 | 2/1989 | Brunetta et al. | 424/63 |
| 4,880,620 | 11/1989 | Vanlerberghe et al. | 424/70 |
| 4,895,876 | 1/1990 | Schweighardt et al. | 514/747 |
| 4,959,171 | 9/1990 | Pantini et al. | 252/174 |
| 5,093,023 | 3/1992 | Pantini et al. | 252/174.23 |
| 5,275,808 | 1/1994 | Murray et al. | 424/70 |

FOREIGN PATENT DOCUMENTS

| | | |
|---|---|---|
| 0486135 | 5/1982 | European Pat. Off. |
| 0148482 | 7/1985 | European Pat. Off. |
| 0191490 | 8/1986 | European Pat. Off. |
| 0195714 | 9/1986 | European Pat. Off. |
| 0196904 | 10/1986 | European Pat. Off. |
| 0560292 | 3/1990 | European Pat. Off. |
| 0512243 | 11/1992 | European Pat. Off. |
| 55-100308 | 7/1980 | Japan |
| 60-34730 | 2/1985 | Japan |
| 63-107911 | 5/1988 | Japan |
| 6801885 | 5/1968 | Netherlands |
| 2052537 | 1/1981 | United Kingdom |
| 88/06434 | 9/1988 | WIPO |

OTHER PUBLICATIONS

Derwent Abstract of EP 0 195 714.
Derwent Abstract of JP 60/34730.
Derwent Abstract of JP 55-100308.

Primary Examiner—Thurman K. Page
Assistant Examiner—Jyothsna Venkat
Attorney, Agent, or Firm—Rimma Mitelman

[57] ABSTRACT

A hair treatment composition comprising from 0.00001 to 0.01% by weight of a perfluoropolyether material.

1 Claim, No Drawings

HAIR TREATMENT COMPOSITION

This is a continuation of Ser. No. 07/753,510 filed Sep. 3, 1991 now U.S. Pat. No. 5,275,808.

BACKGROUND OF THE INVENTION

The present invention relates to hair-treatment compositions, and more particularly to shampoos or conditioning compositions which comprise a perfluoropolyether material.

It is known that oils can provide conditioning benefits such as ease of combing of wet or dry hair, soft feel and improved shine. Generally, however, these materials are only effective at high levels.

The use of perfluoropolyethers of the formula $$F(C_3F_6O-)_n-C_2F_5$$

where n is from 4 to 500, in cosmetics is disclosed in JP 63 10 79 11 (Shiseido).

EP 360 292 (AUSIMONT) relates to the use of 0.01 to 20% by weight of perfluoropolyethers having perfluoroalkyl end groups in foam baths, cleansing milks, bath oils and liquid soaps for the treatment of seborrhea.

BRIEF SUMMARY OF THE INVENTION

Surprisingly, we have found that the condition of hair can be improved by using a hair-treatment composition which contains only low levels of a perfluoro polyether material. In particular it has been found that conditioning benefits to hair can be provided by using a hair-treatment composition which comprises from 0.00001 to 0.01% by weight of a perfluoropolyether material.

Other possible advantages obtained by using low levels of perfluoropolyether materials in hair treatment compositions are: low-risk of over-conditioning, improved cleanliness and interference with sebaceous distribution.

Accordingly, the invention provides a hair treatment composition comprising from 0.00001 to 0.01% by weight of a perfluoropolyether material.

Preferably the hair treatment composition according to the invention is a shampoo or a hair-conditioner.

DETAILED DESCRIPTION OF THE INVENTION

Perfluoropolyether

The hair-treatment composition of the invention comprises a perfluoropolyether material. Suitable perfluoropolyethers and their method of preparation are described in GB 1,104,482, U.S. Pat. No. 3,242,218, U.S. Pat. No. 3,665,041, U.S. Pat. No. 3,715,378, U.S. Pat. No. 4,523,039, EP 148,482 and EP 191,490.

Preferred perfluoropolyether materials are homo- or copolymers of the following formula:

$$F-(C_yF_{2y}O)_n-C_zF_{(2z+1)}$$

wherein
z is an integer from 1 to 6, more preferably 1–3, most preferably 1 or 2;
for each monomer, y is independently selected from the integer-range from 1 to 6, more preferably 1–5, most preferably 1–3;
n indicates the total number of monomers in the polymer backbone and is at least 1, more preferably at least 5, most preferably at least 10

Since y is independently selected for each monomer unit, polymers of the invention may be homopolymers (if for each monomer y is the same) or copolymers (if at least two values of y are chosen for different monomers).

Most preferably n is selected such that the molecular weight of the polymer is from 100–100,000, more preferably 500–50,000, most preferably 1,000 to 10,000.

Particularly preferred end-groups of the perfluoro polyether (PFPE) material are those wherein z is 1 or 2.

Suitable monomer units for use in polymers of the invention are for example disclosed in EP 360 292. Particularly preferred polymer backbone monomers are of the group consisting of:

a) $(CF_2-CF_2-O)$ b) $(CF_2-O)$ c) $(C_3F_6-O)$ d) $(CF-O)$
   $\;\;\;\;|$
   $\;\;\;\;CF_3$ e) $(CF-CF_2-O)$
   $\;\;\;\;|$
   $\;\;\;\;CF_3$ f) $(CF_2-O-CF_2-O)$ g) $(CF_2-O-C_2F_4-O)$;

and mixtures of these monomers.

Particularly preferred polymers comprise a combination of branched polymer unit, for example monomers d) and/or e), with linear monomers, for example a)-c), f) or g). Especially suitable are polymers comprising mixtures of isopropylether groups and methyl ether groups. Especially preferred examples of PFPE materials are those having the formula:

$$CF_3-O-(CF-CF_2-O)_n(CF_2-O)_m-CF_3$$
$$\;\;\;\;\;\;\;\;\;\;\;\;|$$
$$\;\;\;\;\;\;\;\;\;\;CF_3$$

wherein the ratio of n to m is from 20 to 40, and wherein preferably the backbone monomers are randomly distributed along the PFPE chain.

Preferred PFPE materials of this formula are those sold under the trade name FOMBLIN HC by Montefluos. For example, FOMBLIN HC/04 (average molecular weight 1500), FOMBLIN HC/25 (average molecular weight 3200) and FOMBLIN HC/R (average molecular weight 6600).

Other suitable materials are sold under the Demnam trade name ex Daikin Industries Ltd, for example Demnam S-20 having a molecular weight of 2,500, Demnam S-65 having a molecular weight of 4,500, Demnam S-100 having a molecular weight of 5,600 and Demnam S-200 having a molecular weight of 8,400.

If mixtures of backbone monomers are used, preferably the different types of monomers are randomly distributed along the PFPE chain.

The level of PFPE materials in hair treatment compositions of the invention is from 0.00001 to 0.01% by weight of the composition, more preferably 0.0001 to 0.008%, most preferably 0.0001 to 0.005%.

If less than 0.00001% by weight of PFPE is used in the composition, no appreciable improvement in condition will be observed. The use of PFPE levels over 0.01% by weight of the composition provides cost disadvantages, also this may lead to problems in manufacturing and the hair may appear oily or dull, also the use of levels of perfluoropolyethers at higher levels will generally generate the need for suspending agents.

OTHER INGREDIENTS

Preferred hair treatment compositions of the invention comprise one or more surfactant materials and/or one or more conditioning agents.

Shampoo compositions in accordance to the present invention preferably comprise one or more surfactant materials selected from anionic, nonionic, amphoteric or cationic surfactants or mixtures thereof.

Hair conditioning products preferably comprise one or more cationic surfactants. The use of cationic surfactants is especially preferred, because these ingredients are capable of providing conditioning benefits to hair.

Suitable anionic surfactants are the alkyl sulphates, alkyl ether sulphates, alkaryl sulphonates, alkyl succinates, alkyl sulphosuccinates, N-alkoyl sarcosinates, alkyl phosphates, alkyl ether phosphates, alkyl ether carboxylates, and $\alpha$-olefin sulphonates, especially their sodium, magnesium, ammonium and mono-, di- and tri-ethanolamine salts. The alkyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate and sodium N-lauryl sarcosinate. The most preferred anionic surfaceants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

The nonionic surfactants suitable for use in the composition of the invention may include condensation products of aliphatic ($C_8$–$C_{18}$) primary or secondary linear or branched-chain alcohols or phenols with alkylene oxides, usually ethylene oxide and generally 6–30EO.

Other suitable nonionics include mono- or di-alkyl alkanolamides or alkyl polyglucosides. Examples include coco mono- or di-ethanolamide, coco monoisopropanolamide, and coco di-glucoside.

The amphoteric surfactants suitable for use in the composition of the invention may include alkyl amine oxides, alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates and acyl glutamates wherein the alkyl and acyl groups have from 8 to 18 carbon atoms. Examples include lauryl amine oxide, cocodimethyl sulphopropyl betaine and preferably lauryl betaine, cocamidopropyl betaine and sodium cocamphopropionate.

Examples cationate surfactants include: cetyl trimethylammonium chloride, stearyl dimethylbenzyl ammonium chloride, cetylpyridinium chloride, quaternium-5, −31, −18 and mixtures thereof.

The level of surfactant materials in shampoo compositions of the invention is preferably more than 1%, more preferably 2–35% and most preferably from 5 to 30% by weight of the composition. In hair-conditioner products according to the invention the level of cationic surfactants is preferably from 0.01 to 10%, more preferably 0.05 to 5%, most preferably 0.1 to 2% by weight of the composition.

If the hair-treatment composition of the invention comprises in addition to the perfluoropolyether materials and the cationic surfactant -if any- an additional conditioning agent, this material is preferably chosen from cationic polymers, volatile and non-volatile silicones, protein hydrolysates or quaternised protein hydrolysates.

Suitable cationic polymers include Guar Hydroxypropyltrimonium chloride, Quaternium-19, −23, −40, −57, poly (dimethyldiallylammonium chloride), poly (dimethyl butenyl ammonium chloride)-,w- bis (triethanolammonium chloride), Poly (dipropyldiallylammonium chloride), Poly (methyl-beta-propaniodiallyammonium chloride), Poly (diallylpiperidinium chloride), poly (vinyl pyridinium chloride), quaternised poly (vinyl alcohol), quaternised poly (dimethylaminoethylmethacrylate) and mixtures thereof.

Examples of suitable volatile silicone materials include cyclomethicone, available commercially as Dow Corning DC 345, and Volatile Silicone 7158, available form Union Carbide.

Suitable protein derivatives include lauryl dimonium hydroxy propylamino hydrolysed animal protein, available commercially under the tradename LAMEQUAT L, and hydrolysed keratin containing sulphur-bearing amino acids, available commercially under the tradename CROQUAT WKP.

Conditioning agents which are especially suitable for use in shampoos or conditioners according to the invention include volatile and non-volatile silicone oils, such as for example polyalkylsiloxanes, polyalkylaryl siloxanes, silicone gums, cyclomethicones and aminofunctional silicones. Preferably these silicone materials are incorporated in the shampoo conditioner as small particles, preferably of particle size 0.01 to 1 $\mu$m.

The preferred level of conditioning agents other than perfluoropolyethers and cationic surfactants in compositions of the invention is from 0 to 20%, for example from 0.01 to 10% or from 0.1 to 5% by weight.

Another ingredient that may advantageously be incorporated into products of the invention is a fatty alcohol material. The use of these materials is especially preferred in conditioning compositions of the invention, in particular conditioning compositions which comprise one or more cationic surfactant materials. The combined use of fatty alcohol materials and cationic surfactants in conditioning compositions is believed to be especially advantageous, because this leads to the forming of a lamellar phase, wherein the cationic surfactant is dispersed. Preferred fatty alcohols comprises from 8 to 22 carbon atoms, more preferably 16 to 20. Examples of preferred fatty alcohols are cetyl alcohol and stearyl alcohol. The use of these materials is also advantageous in that they contribute no the overall conditioning properties of compositions of the invention.

The level of fatty alcohol materials is conveniently from 0 to 10%, more preferred from 0.1 to 5% by weight of the product. The weight ratio of cationic surfactant to fatty alcohol is preferably from 10:1 to 1:10, more preferably from 4:1 to 1:8, most preferably from 1:1 to 1:4.

Minor Ingredients

The hair-treatment composition of the invention may also include minor amounts of other ingredients commonly found in hair-treatment compositions, such as antibacterial agents, antidandruff agents such as zinc pyridinethione or Octopirox, foam boosters, pearlescers, perfumes, dyes, colouring agents, preservatives, viscosity modifiers, proteins, polymers, buffering agents, polyols and other moisturising agents, herb extracts, mink oil or honey.

Water

Compositions of the invention preferably comprise from 20–99.5% of water, more preferably 60–98%, most preferably 80–96% by weight.

USE OF THE COMPOSITION

After preparation, hair treatment compositions according to the invention are preferably packed. Any suitable container can be used for this purpose, but generally compositions of the invention will be packed in closed containers like bottles, sachets and the like.

Hair treatment compositions of the invention are generally applied in an amount of from 1 to 50 mls. Preferred amounts for shampoos are 3 to 5 mls to wet hair. After applying the shampoo the wet hair is worked to create a lather. The lather may be retained on the head for a short time before rinsing, e.g. from 1 to 4 minutes, or may immediately be rinsed. The treatment may be repeated, if required. For conditioners the preferred dosage is from 8 to 20 mls which is applied to hair after washing or rinsing, whereafter the wet hair is worked and rinsed.

In preparing hair-treatment compositions of the invention, preferably conventional hot or cold mixing processes are used. Preferred methods for adding the PFPE ingredient to the compositions are the forming of a predispersion of PFPE with small amounts of surfactants in combination with a thickening amount of electrolyte, or a predispersion can be formed of PFPE with polymer ingredients, or a predispersion of PFPE with low levels of surfactant in combination with glycerol. This predispersion is than used in the preparation of the final hair-treatment composition.

The invention is further illustrated by the following Examples:

Example I

The following conditioner compositions can be made by heating the water to 80° C. The first five ingredients are added with stirring. The mixture is cooled to 40° C. with stirring. Preservatives, perfume and colour are added. The resulting mixture is cooled.

| INGREDIENT | % wt |
| --- | --- |
| Cetyl trimethylammoniumchloride | 0.7 |
| Cetostearyl alcohol | 2.0 |
| Paraffin wax | 1.0 |
| Glycerolmonostearate | 0.7 |
| PFPE *) | 0.001 |
| Preservative, perfume, colour | qs |

| INGREDIENT | % wt |
| --- | --- |
| water | to 100 |

*)Demnam S-20, S-65, S-100 or S-200.

Example II

A shampoo of the following forumulation can be made by using a simple cold process, whereby all the ingredients are mixed using a paddle stirrer.

| INGREDIENT | % wt |
| --- | --- |
| Sodium Lauryl ether sulphate 2EO | 16.0 |
| Lauryl betaine | 2.0 |
| Jaguar C13S | 0.04 |
| PFPE[1] | 0.003 |
| NaCl | 1.0 |
| Preservative, perfume, colour | qs |
| water | to 100 |

[1]Demnam S-20, S-65, S-100 or S-200, or Fomblin HC/04, Fomblin HC/25 or Fomblin HC/R.

The composition containing Fomblin HC/04 was tested in vitro on hair by wetting 8 g of hair, lathering it for 30 s with 0.5 ml of shampoo, leaving it for another 20 s and rinsing with water; the procedure was repeated but using 0.4 g of the shampoo, the hair was dried. As a comparison the hair was treated with the above composition in the absence of PFPE.

The evaluation was carried out by twelve trained assessors in the form of paired comparison test. The results were interpreted statistically at 0.01 and 0.05 confidence levels. Softness was assessed by feel. Shine was assessed by viewing the hair switches mounted over a curved surface under a spotlight to create a highlight which was then visually assessed for its light intensity.

The hair treated with the composition according to the invention had a significantly better condition, especially as far as dry-combing and shine is concerned. Similar results may be obtained by using the other PFPE materials as indicated above.

Example III

The following formulations can be made as in Example II.

| INGREDIENT | % wt |
| --- | --- |
| Sodium Lauryl ether sulphate 2EO | 16.0 |
| Cocobetaine (Empigen BB ex A&W) | 6.6 |
| PFPE[1] | 0.005 |
| NaCl | 1.0 |
| preservative, perfume, colour | qs |
| water | to 100 |

[1]Demnam S-20, S-65, S-100 or S-200, or Fomblin HC/04, Fomblin HC/25 or Fomblin HC/R.

The composition containing Fomblin HC/R was tested in vitro on hair by a method as described in example II. As a comparison the hair was treated with the above composition in the absence of PFPE. The hair treated with the composition according to the invention had a significantly better condition, especially as far as dry-combing and shine is concerned. Similar results may be obtained by using the other PFPE materials as indicated above.

Example IV

The following shampoo formulations can be made as in Example II.

| INGREDIENT | % wt |
| --- | --- |
| Alpha olefin sulphonate (Elfan OS45 ex AKZO) | 10.0 |
| PFPE[1) | 0.007 |
| Methocell E4 | 1.0 |
| Preservative, perfume, colour | qs |
| water | to 100 |

[1)Demnam S-20, S-65, S-100 or S-200, or Fomblin HC/04, Fomblin HC/25 or Fomblin HC/R.

Example V

The following shampoo formulations can be made as in Example II.

| INGREDIENT | % wt |
| --- | --- |
| Triethanolamine lauryl sulphate | 12.0 |
| PFPE[1) | 0.001 |
| Jaguar HP 60 | 1.0 |
| preservative, perfume, colour | qs |
| water | to 100 |

[1)Demnam S-20, S-65, S-100 or S-200, or Fomblin HC/04, Fomblin HC/25 or Fomblin HC/R.

Example VI
The following formulation was manufactured as in Example I.

| INGREDIENT | % wt |
| --- | --- |
| cetyl trimethyl ammonium chloride | 1.0 |
| ceto stearyl alcohol | 1.5 |
| Natrosol 250 HR | 1.5 |
| PFPE[1) | 0.001 |
| silicone emulsion[2) | 1.0 |
| preservative, perfume, colour | qs |
| water | to 100 |

[1)Demnam S-20, S-65, S-100 or S-200
[2)Silicone emulsion BY 22-026 from Toray Silicone Co. Ltd.

Example VII

The following formulations can be made as in Example II.

| INGREDIENT | % wt |
| --- | --- |
| Sodium lauryl sulphate | 5.0 |
| Alkyl polyglucoside | 12.0 |
| Polyethylene glycol 6000 distearate | 0.3 |
| PFPE[1) | 0.003 |
| Sodium chloride | 0.5 |
| Preservative, buffer, perfume | qs |
| Water | to 100 |

[1)Demnam S-20, S-65, S-100 or S-200, or Fomblin HC/04, Fomblin HC/25 or Fomblin HC/R.

Example VIII

The following formulations A, B, C and D were made and tested as described in Example II. Formulation A was a control, Formulations B and C were in accordance with the present invention, Formulation D was not in accordance with the invention. All amounts are in % wt, unless otherwise stated.

| INGREDIENT | A (control) | B | C | D |
| --- | --- | --- | --- | --- |
| Sodium lauryl ether sulphate 2EO | 12.0 | 16.0 | 16.0 | 16.0 |
| Cocobetaine (Empigen BB ex A&W) | — | 6.6 | 6.6 | 6.6 |
| Formalin (40%) | 0.2 | 0.2 | 0.2 | 0.2 |
| Fomblin HC/04 | — | 0.001 | 0.003 | 0.03 |
| Jaguar C13S | — | 0.04 | 0.04 | 0.04 |
| Sodium chloride | 1.1 | 1.1 | 1.1 | 1.1 |
| Water | to 100 | to 100 | to 100 | to 100 |

A paired comparison test of shine properties of Formulation A versus each of Formulations B, C and D gave the following results:

| | % votes for test forumulations | |
| --- | --- | --- |
| A vs B | 68 | (>99%)· |
| A vs C | 71 | (>99%)· |
| A vs D | 49 | |

·significance level

Example IX

The following formulations E, F and G were made and tested as described in Example II. Formulation E was a control, Formulation F was in accordance with the present invention, Formulation G was not in accordance with the invention. Amounts are in % wt, unless otherwise stated.

| INGREDIENT | E (control) | F | G |
| --- | --- | --- | --- |
| 50% Cetyltrimethyl-ammoniumchloride[1) | 1.4 | 1.4 | 1.4 |
| Cetostearyl alcohol[2) | 1.0 | 1.0 | 1.0 |
| Hydroxyethylcellulose[3) | 1.3 | 1.5 | 1.5 |
| Formalin | 0.2 | 0.2 | 0.2 |
| Fomblin HC/04 | — | 0.001 | 0.03 |
| Water | to 100 | to 100 | to 100 |

[1)Arquad 16-50
[2)Laurex CS
[3)Natrosol 250 HR

A paired comparison test of shine properties of Formulation E versus each of Formulations F and G gave the following results:

| | % votes for test formulations | |
| --- | --- | --- |
| E vs F | 72 | (>99%)· |
| E vs G | 14 | |

·significance level

We claim:
1. A hair treatment composition comprising from
   (a) 0.00001 to 0.003% by weight of a perfluoropolyether material, wherein the perfluoropolyether material has the following formula: $F-(C_yF_{2y}O)_n-C_zF_{(2z+1)}$ wherein z is an integer from 1 to 6, for each monomer, y is independently selected from the integer range from 1 to 6, n indicates the total number of monomers in the polymer backbone, and n is such that the molecular weight of the perfluoropolyether material is from 100–100,000; and
   (b) from 2 to 35% by weight of a surfactant.

* * * * *